United States Patent
Zhang et al.

(10) Patent No.: US 9,694,115 B2
(45) Date of Patent: Jul. 4, 2017

(54) MANUFACTURING METHOD OF IRON-BASED ALLOY MEDICAL APPARATUS

(71) Applicant: Lifetech Scientific (Shenzhen) Co., Ltd., Shenzhen (CN)

(72) Inventors: Deyuan Zhang, Shenzhen (CN); Wenbin Wang, Shenzhen (CN); Ziqiang Liu, Shenzhen (CN)

(73) Assignee: Lifetech Scientific (Shenzhen) Co. Ltd., Shenzhen (CN)

( * ) Notice: Subject to any disclaimer, the term of this patent is extended or adjusted under 35 U.S.C. 154(b) by 0 days.

(21) Appl. No.: 14/894,088

(22) PCT Filed: May 28, 2014

(86) PCT No.: PCT/CN2014/078663
§ 371 (c)(1),
(2) Date: Nov. 25, 2015

(87) PCT Pub. No.: WO2014/190908
PCT Pub. Date: Dec. 4, 2014

(65) Prior Publication Data
US 2016/0121028 A1    May 5, 2016

(30) Foreign Application Priority Data

May 30, 2013 (CN) .......................... 2013 1 0210113

(51) Int. Cl.
*C23F 1/00* (2006.01)
*A61L 31/02* (2006.01)
(Continued)

(52) U.S. Cl.
CPC ........... *A61L 31/022* (2013.01); *A61L 31/148* (2013.01); *A61L 31/16* (2013.01); *C23C 8/02* (2013.01);
(Continued)

(58) Field of Classification Search
CPC ...... C23F 1/00; C23F 1/12; C23F 1/26; C23F 1/28; A61L 31/16; A61L 33/00; A61L 31/148; A61L 31/022; C23C 8/38
(Continued)

(56) References Cited

U.S. PATENT DOCUMENTS

| 5,443,663 A * | 8/1995 | Meletis | ..................... C23C 8/36 148/222 |
| 6,110,571 A * | 8/2000 | Yaginuma | ................. C23C 8/38 428/216 |

(Continued)

*Primary Examiner* — Lan Vinh
(74) *Attorney, Agent, or Firm* — Raymond Sun

(57) ABSTRACT

Disclosed is a manufacturing method of an iron-based alloy medical apparatus, comprising: nitriding the iron-based alloy preformed unit at 350-550° C. for 30-100 minutes; and ion etching the iron-based alloy preformed unit with an ion etching time of 80-110% of the nitriding time. Ion nitriding and ion etching can be performed in situ in the same equipment using this manufacture method with high production efficiency, and in the ion nitriding and ion etching process, nitrogen atoms continuously permeate the preformed unit, making the time it takes for the medical apparatus to be absorbed by the human body and both the hardness and strength of the instrument surface achieve requirements.

8 Claims, 2 Drawing Sheets

(51) Int. Cl.
 *A61L 31/14* (2006.01)
 *A61L 31/16* (2006.01)
 *C23C 8/02* (2006.01)
 *C23C 8/26* (2006.01)
 *C23C 8/38* (2006.01)
 *C23C 8/80* (2006.01)
 *H01J 37/00* (2006.01)
(52) U.S. Cl.
 CPC ............... *C23C 8/26* (2013.01); *C23C 8/38* (2013.01); *C23C 8/80* (2013.01); *C23F 1/00* (2013.01); *H01J 37/00* (2013.01)
(58) Field of Classification Search
 USPC ........ 216/58, 59, 77, 78; 438/710, 712, 714, 438/720
 See application file for complete search history.

(56) References Cited

U.S. PATENT DOCUMENTS

| | | | |
|---|---|---|---|
| 6,375,826 B1* | 4/2002 | Wang | C25F 7/00 204/224 M |
| 2007/0190231 A1* | 8/2007 | Chandrasekaran | A61F 2/91 427/2.25 |
| 2008/0206441 A1* | 8/2008 | Krivoruchko | A61F 2/0077 427/2.25 |
| 2011/0214785 A1* | 9/2011 | Buckman, Jr. | B21D 31/00 148/237 |

* cited by examiner

MANUFACTURING METHOD OF IRON-BASED ALLOY MEDICAL APPARATUS

TECHNICAL FIELD

The present invention relates to the field of interventional medical apparatuses, and in particular to a manufacturing method of an iron-based alloy medical apparatus by nitriding and ion etching.

BACKGROUND OF THE INVENTION

With the improvement of people's living standard, the dietary structure is changed, the incidence of cardiovascular diseases becomes higher and higher, and the coronary heart disease caused by cardiovascular stenosis has become a main disease dangerous to human health. The percutaneous transluminal coronary angioplasty procedure is the primary method of treating coronary atherosclerotic heart disease. Since 1977, through nearly three decades of continuous development and improvement, the interventional treatment for coronary heart diseases has been constantly improved in the technological level and has totally experienced three eras, i.e., Balloon Dilatation (PTCA), Bare Metal Stents (BMS) and Drug Eluting Stents (DES).

At present, coronary stents commonly used in the clinic are classified into two categories, i.e., bare metal stents and drug eluting stents. Although DESs may reduce the rate of restenosis and repeat revascularization, but existing polymer carrier drug eluting stents still have certain limitations. These limitations are mainly manifested as late and very-late stent thrombosis, endothelial healing delay and late catch-up of luminal loss. However, the main reason is inflammatory reaction caused by polymer carriers. This problem and effective means for solving this problem have always been widely disputed in international research fields. When the restenosis occurs, a stent is unable to be implanted secondarily as it is disadvantageous to the late angioplasty. Therefore, it is desirable to research and develop biodegradable stents.

Biodegradable stents have become a hotspot of research and development. For example, taking an iron-based alloy vessel stent for an example, by surface alloying the iron-based alloy stent, for example, nitriding from a surface to inside to form a readily-corrodible diffusion layer having high hardness, the strength of the stent is improved, the corrosion rate of the stent is quickened, and the absorption period of the stent is shortened. However, the stent is very likely to form a dense $\epsilon$-phase or $\gamma'$-phase compound layer (commonly known as a white bright layer) having high nitrogen content on its surface during nitriding. This compound layer has relatively stable chemical properties, is able to resist the corrosion of acidic or alkaline solution, and is difficult to be corroded in a human tissue. If the compound layer cannot be effectively removed during the process of manufacturing the iron-based alloy vessel stent, the corrosion rate of the stent will be greatly affected, and the absorption period of the stent is thus prolonged.

At present, removing this compound layer may be performed by mechanical polishing, electrochemical polishing, vacuum denitriding, and ion nitriding at a low nitrogen potential. However, these methods all have some defects.

Although the mechanical polishing may quickly remove the white bright layer, a fine implant medical instrument, for example, a very small strut of a vessel stent, has very strict dimensional tolerances (e.g., a precision of 5 μm). The dimensional precision of such a medical instrument cannot be ensured if the mechanical polishing is used, that is, the fine medical instrument is unable to employ this method.

The electrochemical polishing needs to use strong acids or other solutions, so it is very likely to result in the corrosion defect of the surface of a nitriding layer of a medical instrument after the compound layer is removed. Meanwhile, the surface of a diffusion layer of the fine medical instrument may become bright and flat only after the removal amount of polishing (a difference in the thickness of the medical instrument before and after polishing) reaches 40 μm, so that the compound layer closest to the surface will be removed, and a part of the diffusion layer will also be removed. As a result, the remaining diffusion layer will be very thin, which is disadvantageous to the quality control of a thin-wall portion (e.g., a strut of a vessel stent) of the medical instrument.

The vacuum denitriding may facilitate the change of a phase structure by changing ambient pressure and temperature, thereby realizing the desorption (retroaction of adsorption) of nitrogen in the compound layer and the diffusion layer. If the temperature holding time is long enough (6-9 hours), the nitrogen concentration of the surface may be reduced so that the compound layer is reduced or eliminated. However, actually, as the required temperature holding time is too long, the escape of nitrogen atoms will influence the diffusion layer of a vessel stent and thus reduce the surface hardness, but there are still few compound layers on the surface of the vessel stent. Therefore, this method is unable to really effectively remove the compound layer, and will reduce in turn the performance of the stent.

Theoretically, during nitriding at a low nitrogen potential, when the actual nitrogen potential does not exceed a particular threshold during nitriding, the compound layer will not be formed. However, this method greatly restrains the permeation rate of nitrogen atoms, so the nitriding efficiency is greatly reduced. As a result, a very long temperature holding and diffusion time is required to form a desired nitriding layer. Due to the fact that the dispersed phase in the nitriding layer is gathered and grown, both the hardening effect and galvanic corrosion effect of the dispersed phase are weakened, and the basic performance of the iron-based alloy medical instrument is thus reduced.

Therefore, it is necessary to provide a manufacturing method, which gives consideration to both product performance and manufacturing efficiency, which quickly and effectively removes a compound layer formed on an iron-based alloy medical apparatus after nitriding, and which meets the performance requirements of a biological medical apparatus.

DISCLOSURE OF THE INVENTION

Technical Problem

An object of the present invention is to provide a manufacturing method of an iron-based alloy medical apparatus, which may quickly and effectively remove a compound layer, giving consideration to both performance requirements and manufacture efficiency of the medical apparatus.

Technical Solution

To achieve the object of the present invention, a technical solution is employed: step 1, a preformed unit of an iron-based alloy medical apparatus is manufactured; step 2, the surface of the performed unit is cleaned; step 3, the preformed unit is heated to 350-550° C., and the surface of the preformed unit is nitrided for 30-100 minutes; and, step 4, the preformed unit is ion-etched with an ion etching time of 80-110% of the nitriding time.

In an embodiment of the present invention, step 5, i.e., polishing the ion-etched preformed unit, may be added after step 4.

In an embodiment of the present invention, step 6, i.e., forming a drug-loaded coating on the surface of the preformed unit, may be further added after step 5.

In step 1 of an embodiment of the present invention, an operation frequency of 300-1000 Hz, an operation voltage of 200-300 V, a pulse width of 0.02-0.18 μs and a cutting speed of 0.05-0.3 inch/s of a laser cutting machine are set. Taking manufacturing an iron-based alloy stent as an example, during cutting tubes, it is required to control an oxygen pressure to be greater than 3 atm, an air pressure to be greater than 2.5 atm, and a cooling water pressure to be greater than 20-50 psi (2.5 kg/cm$^2$). In step 2, the cleaning is first ultrasonically cleaning the stent for 1-3 minutes with water, then ultrasonically cleaning the stent for 5-30 minutes with absolute ethyl alcohol, and ultrasonically cleaning the stent for 1-3 minutes with an acidic solution.

In an embodiment of the present invention, the surface hardness of the preformed unit in step 1 is 165-175 HV.

In an embodiment of the present invention, the preformed unit in step 1 is above 20 μm thicker than the preformed unit after step 4, and a surface thickness of above 15 μm of the preformed unit is removed in step 5.

In an embodiment of the present invention, the preformed unit in step 1 is 30-60 μm thicker than a medical apparatus or medical component manufactured by this method.

In an embodiment of the present invention, the cleaning in step 2 is normal-temperature chemical polishing and cleaning. The cleaning includes a step of soaking the preformed unit in a chemical polishing solution for 5-10 seconds. A formulation of 100 parts of the chemical polishing solution is as follows: 75-85 parts of hydrogen peroxide having a volume concentration of 30%, 3-7 parts of hydrofluoric acid having a volume concentration of 40%, and the rest being purified water or substantially water.

In an embodiment of the present invention, the nitriding in step 3 includes ion nitriding. A mixed gas of nitrogen and hydrogen is employed, with a flow ratio of nitrogen to hydrogen being 1:2 to 1:9, and the gas is discharged at an atmospheric pressure of 40-150 Pa and at a bias voltage of 600-650 V.

In an embodiment of the present invention, the temperature of the preformed unit in step 4 is 500-550° C.

In an embodiment of the present invention, the ion etching in step 4 is as follows: a mixed gas of argon and hydrogen is employed, with a flow ratio of argon to hydrogen being 1:2 to 1:9, and the gas is discharged at an atmospheric pressure of 20-120 Pa and at a bias voltage of 650-800 V.

In an embodiment of the present invention, the flow ratio of argon to hydrogen in step 4 is 1:3 to 1:7, and the gas is discharged at an atmospheric pressure of 40-100 Pa and at a bias voltage of 650-750 V.

In an embodiment of the present invention, after the preformed unit is ion-etched, the surface roughness of the ion-etched preformed unit does not exceed 0.05 μm.

In en embodiment of the present invention, after the preformed unit is ion-etched, there is no a compound layer on its surface.

In an embodiment of the present invention, the polishing in step 5 is normal-temperature chemical polishing, with the polishing time being 30-40 seconds. The formulation of the polishing solution used by the normal-temperature chemical polishing is as follows: by volume, per 100 parts, 75-85 parts of hydrogen peroxide having a volume concentration of 30%, 3-7 parts of hydrofluoric acid having a volume concentration of 40%, and the rest being purified water or substantially water.

In an embodiment of the present invention, an outer layer thickness of 15-30 μm of the performed unit is removed by the normal-temperature chemical polishing.

In an embodiment of the present invention, the nitriding and the ion etching are performed within 4 hours and performed in situ in the same equipment.

Beneficial Effects

Compared with the prior art, the method of manufacturing an iron-based alloy medical apparatus provided by the present invention further employs an ion etching process after the iron-based alloy medical apparatus preformed unit is treated by nitriding. The two processes may be performed in situ in the same equipment as long as equipment parameters are slightly adjusted, with high production efficiency. In the ion nitriding and ion etching, nitrogen atoms continuously permeate the medical apparatus, allowing it to achieve requirements such as the time it takes for the medical apparatus to be absorbed by the human body, and both the hardness and strength of the instrument surface. The iron etching may also effectively remove a corrosion-resistant compound layer formed by the ion nitriding. In addition, this method also reduces the difficulty of a subsequent polishing step, so that the normal-temperature chemical polishing easily achieves mirror polishing effects and conforms more to the medical and production safety requirements.

DETAILED DESCRIPTION OF THE INVENTION

Figure 1:
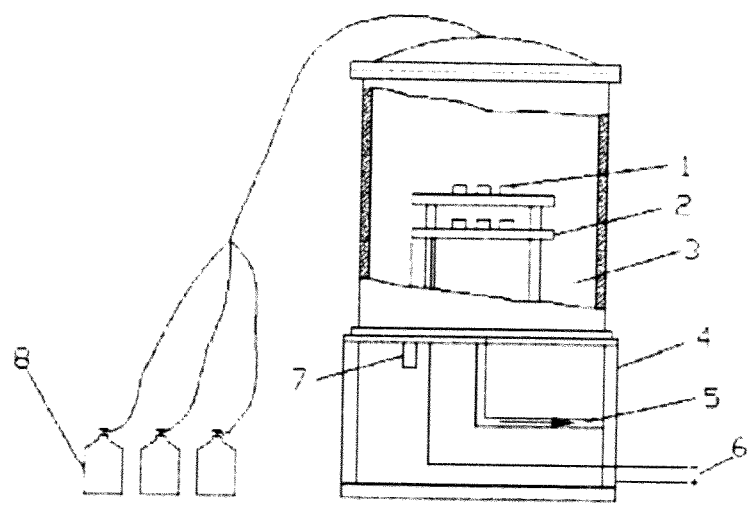
FIG. 1 is a schematic diagram of an apparatus used by a manufacturing method according to the present invention.

To make the object, technical solutions and advantages of the present invention clearer, the present invention will be further described below in detail with reference to the accompanying drawings and embodiments. It should be understood that the specific embodiments described herein are merely for explaining the present invention and are not intended to limit the present invention.

The method of manufacturing an iron-based alloy medical apparatus provided by the present invention includes an ion nitriding step and an ion etching step. The nitriding is first performed by using a mixed gas of nitrogen and hydrogen, and the ion etching is then performed by using a mixed gas of argon and hydrogen. In the ion etching step, nitrogen atoms near the surface of the medical apparatus continuously diffuse to the inside of the medical instrument. In the ion etching step, a low atmospheric pressure and an appropriate temperature of the medical apparatus are maintained, argon ions and hydrogen ions are generated by ionizing a mixed gas of argon and hydrogen by a high voltage electric field (600-800 V), and the effect of quickly removing a compound layer formed in the ion nitriding step is achieved by argon ion sputtering. The hydrogen ions increase the inter-collision and ionization reaction between gas molecules, and may also increase the yield of argon ions under a low atmospheric pressure, improve the surface current density and surface atom sputtering rate of the medical apparatus and avoid arc discharge. Meanwhile, the hydrogen ions have a very strong reduction capability, thereby facilitating the decomposition of oxides in a surface layer of the medical apparatus (the oxygen-containing impurities in the nitrogen raw material and a vacuum chamber are likely to enter the surface layer). A part of the decomposed and separated out nitrogen atoms is diffused to the inside of the diffusion layer of the medical apparatus, while another part of the nitrogen atoms is sputtered into the surrounding gas environment by the argon ions. The reduction of the nitrogen atoms in the surface layer will convert high-nitrogen compounds into low-nitrogen compounds, thereby quickly reducing the thickness of the compound layer and meanwhile continuously changing the structure of the diffusion layer at an appropriate temperature.

The iron-based alloy medical apparatus includes finally commercially available medical apparatus products, preformed units formed in the process of manufacturing finally commercially available medical apparatus products, and a certain component of a medical apparatus product and preformed unit thereof. The surface hardness of the preformed unit may be 165-175 HV. The medical apparatus includes a coronary stent, a peripheral stent, a non-vessel stent, and other implant instruments (e.g., occluders) or components of the implant medical instruments. The medical apparatus is made of an iron-based alloy. The iron-based alloy includes pure iron, medium carbon steel, low carbon steel and a medical iron-based alloy. Nutrient elements and harmless elements in human body, or low-toxicity elements, for example, Mn, Pd, Si, W, Ti, Co, Cr, Cu and Re, may be doped in the pure iron to form medical iron-based alloys.

Based on the method provided by the present invention, in the ion etching step, nitrogen atoms continue to diffuse into the inside. As both the ion nitriding step and the ion etching step have a nitriding process, the nitriding time is an addition of the nitriding time and the ion etching time. Taking a preformed unit of a vessel stent for an example, according to the performance requirements for an absorbable vessel stent, the ion nitriding time may be selected from 30 to 100 minutes. The ion etching time is related to the thickness of the compound layer. The thicker the compound layer is, and the longer the required ion etching time is. The experimental data indicates that the ion etching time should be 80%-110% of the ion nitriding time (within 100 minutes), so that a very thin (an average thickness of less than 1 µm) discontinuous compound layer remains on the surface of the preformed unit or the compound layer is completely removed. Thus, it is advantageous to the subsequent process: the mirror polished medical apparatus may be obtained only by a normal-temperature chemical polishing step, and both the mechanical performance and processing precision requirements of the bioabsorbable stent may be met. Therefore, the actual nitriding time may be limited within 4 hours. For a medical apparatus having low requirements in surface roughness, after the compound layer is removed by ion etching, the subsequent polishing step is optional.

Referring to FIG. 1, the apparatus used by the present invention includes a vacuum chamber 3. An anode of a bias power supply 6 is connected to the vacuum chamber 3 of the apparatus. Of source, an anode, which substantially does not hinder gas flow, may be provided near a workpiece rest 2, and the preformed unit is connected to a cathode of the bias power supply 6. Gases 8 required by ion nitriding and ion etching are provided outside the vacuum chamber 3 in tanks. One end of a temperature sensor 7 is fixed, while the other end thereof is near the workpiece rest 2.

A general process of the ion nitriding step is as follows: the vacuum is pumped out till below 10 Pa, a mixed gas of $N_2$ and $H_2$ is slowly fed, and the atmospheric pressure remains stable and may be selected from 40 to 150 Pa. In an embodiment of the present invention, the atmospheric pressure ranges, for example, from 50 Pa to 100 Pa. The bias power supply 6 is activated to remain abnormal glow discharge on the surface of the stent, and the nitrogen ions generated by ionizing the mixed gas bombard the surface of the preformed unit to make the temperature of the surface of the preformed unit rise. The flow ratio of $N_2$ to $H_2$ may range from 1:2 to 1:9. The mixed gas may also be replaced with $NH_3$ or a mixed gas of $H_2$ and $NH_3$, and the glow discharge is performed at an approximately same bias voltage and a corresponding atmospheric pressure in this industry. If the nitriding temperature of the iron-based alloy medical apparatus is too high, the dispersed phase in the diffusion layer will be gathered and grown, so that the hardening action and galvanic corrosion effect caused by the dispersed phase are reduced, and the basic performance of the iron-based alloy medical apparatus is also reduced. When the nitriding temperature is too low (below 350° C.), it is disadvantageous to shorten the ion nitriding time. Therefore, the nitriding temperature of the iron-based alloy vessel stent is 350-550° C. To quickly heat the stent up to a desired temperature, the workpiece rest 2 may be heated by an auxiliary heating device so as to indirectly heat the preformed unit, and it is also possible to preheat the workpiece rest 2 before activating the bias power supply. By adjusting the power of the auxiliary heating device to stabilize the temperature of the preformed unit, the discharge of the gas is also stable. In this case, the bias voltage may range from 400 V to 700 V, preferably, from 600 V to 650 V.

After the nitriding process is finished, a compound layer will be generally formed on the surface of the preformed unit. At this moment, a nitrogen valve is turned off, and preferably the bias power supply 6 is also turned off. Then, the ion etching is started. A mixed gas of argon and hydrogen is slowly fed, the atmospheric pressure remains stable and may be selected from 20 Pa to 120 Pa. Preferably, the atmospheric pressure ranges for example from 40 Pa to 100 Pa. The bias power supply is activated, and the bias voltage may range from 650 V to 800 V. The glow discharge is performed on the surface of the preformed unit, and argon ions and hydrogen ions generated by ionizing the gas quickly decompose the compound layer on the surface of the preformed unit under the simultaneous action of bombardment of argon ions, reduction of hydrogen ions and heat diffusion. By adjusting the power of the auxiliary heating device, the highest temperature of the preformed unit is 350-550° C. The flow ratio of argon to hydrogen in the mixed gas may be selected from 1:2 to 1:9.

After the ion etching process is finished, the preformed unit may be optionally further polished if very few white bright layers remain on the surface of the preformed unit. The polishing may be normal-temperature chemical polishing, with the polishing time being 30-40 seconds. The formulation of the polishing solution used by the normal-temperature chemical polishing is as follows: by volume, every 100 parts, 75-85 parts of hydrogen peroxide having a volume concentration of 30%, 3-7 parts of hydrofluoric acid having a volume concentration of 40%, and the rest being purified water or substantially water. An outer layer thickness of 15-30 μm of the performed unit may be removed by the normal-temperature chemical polishing.

For a drug-loaded iron-based alloy medical apparatus, a drug-loaded coating treatment may further be performed on the surface of the preformed unit. The drug-loaded coating is mainly formed from a degradable carrier and a drug, wherein the degradable carrier may include polylactic acid, lactic acid-glycolic acid copolymer, polyethylene glycol/polylactic acid, choline phosphate, polyhydroxybutyrate, polyhydroxybutyrate-hydroxyvalerate copolymer, polycaprolactone and other polymer high-molecular materials, or may also be chitosan, modified chitosan, choline, phospholipids, collagen and other biological materials. The drug can include drugs for resisting inflammation, suppressing proliferation or promoting endothelial climb. For example, these drugs may be sirolimus, tacrolimus, everolimus, paclitaxel and derivatives thereof.

The specific operation may be as follows: the drug and the carrier may be mixed and dissolved in an organic solvent in proportion, with a mass ratio of the drug to the carrier being 1:4 to 4:1. The used organic solvent may be tetrahydrofuran, dichloromethane, chloroform, methanol or ethanol. After the drug and the carrier are dissolved, drug coating is performed. The coated preformed unit is dried in a dryer at 50T.

A surface coating treatment may be further performed to the drug-loaded coating of the stent, mainly for purpose of controlling a drug release speed and improving the biocompatibility of the coating surface. The coating may be chitosan, modified chitosan, choline, phospholipids, collagen and other biological materials, or a high polymer for improving the hydrophilicity of the surface of the preformed unit. A method for forming the coating may be spraying or dip-coating.

Embodiment 1

In this embodiment, taking manufacturing a pure iron vessel stent for an example, the method of manufacturing an iron-based alloy medical apparatus provided by the present invention will be illustrated. First, according to a typical stent grid design in this industry, the surface of a pure iron tube is carved by lasers to pre-form a pure iron vessel stent having an outer diameter of 3.6 mm, an original wall thickness of 220 μm and a length of 18 mm. When this stent is balloon-dilated to 12 mm, the coverage rate of the metal grid on the surface of the stent to the side wall of the stent is about 9.6%. Second, the preformed pure iron stent is chemically polished and cleaned: the pure iron stent is soaked in a chemical polishing solution, then slightly stirred and shaken, and taken out after about 5-10 seconds. A formulation of 100 parts of the chemical polishing solution is as follows: 75-85 parts of hydrogen peroxide having a volume concentration of 30%, 3-7 parts of hydrofluoric acid having a volume concentration of 40%, and the rest being purified water or substantially water. The polishing is performed at a normal temperature of 20-30° C., for example, at 24-26° C. The chemical polishing solution neither contained any strong acid nor any heavy metal or other harmful constituent, so the chemical polishing solution meets the medical and production safety requirements. The polished vessel stent is neutralized with sodium hydroxide having a mass concentration of 5%-10%, then ultrasonically cleaned for two times with purified water with the time of each ultrasonic cleaning being 10 seconds, and finally dehydrated with absolute ethyl alcohol for storage. After the cleaning step, the wall thickness of the pure iron stent is reduced by about 5 μm (inner and outer walls were reduced by 3.5 μm and 1.5 μm, respectively) for purpose of completely removing contaminants (including oxides) on the surface of the pure iron stent and ensuring the effects of the subsequent processing steps. The experiments showed that, if the surface of the stent was reduced by 1.5-3 μm in thickness, a fresh and clean surface might be ensured, so that the outer surface of the pure iron-based material is completely exposed.

Figure 2:
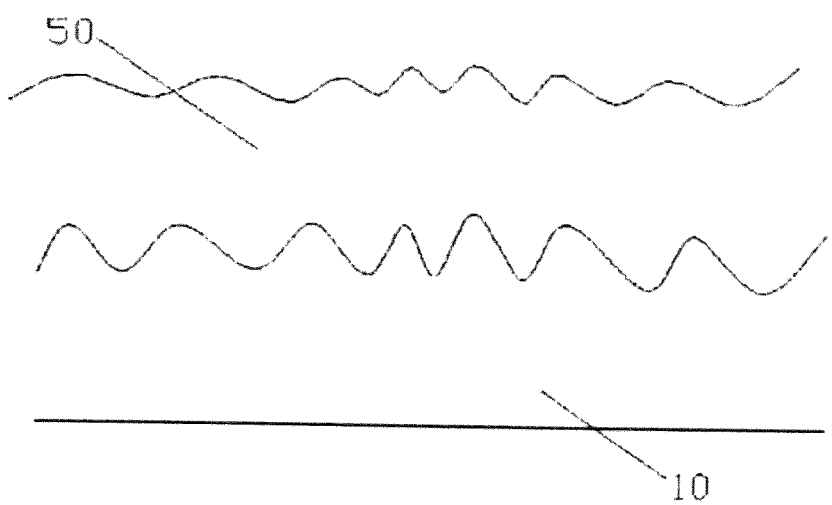
FIG. 2 is a cross-sectional diagram of a vessel stent after ion nitriding according to an embodiment of the present invention.

A surface nitriding treatment is performed on the cleaned pure iron stent, and then the stent dehydrated with absolute ethyl alcohol after cleaning is placed on an insulating workpiece rest of an ion nitriding apparatus. During ion nitriding, a certain thickness of dense and nitrogen-rich white bright layer 50 (i.e., a compound layer) is formed on the surface of the stent. Nitrogen atoms in the white bright layer 50 diffuses to the inside of the stent at a high temperature to form a diffusion layer 10, and the corrosion resistance of the white bright layer 50 far exceeds that of the diffusion layer 10 containing few nitrogen. The partial cross section of the stent is as shown in FIG. 2, where the surface roughness was about 0.2 μm after tested. As the stent material is a polycrystalline metal and a very irregular crystal boundary is spread over the stent material, nitrogen atoms (ions) near the outer surface of the white bright layer 50 are likely to permeate in the diffusion layer 10 from the crystal boundary so as to generate nitrides, so that the boundary of the white bright layer 50 and the diffusion layer 10 is advanced to the inside and this boundary fluctuates like a hill. The concentration of nitrogen atoms of the white bright layer 50 is high while the concentration of nitrogen atoms in the diffusion layer 10 is very low, the nitrogen atoms certainly diffuses from the white bright layer 50 to the inside of the diffusion layer 10. The distribution of nitrogen atoms depends on the chemical potential, diffusion coefficient, temperature and time. In this embodiment, the following ion nitriding parameters are selected: a stent temperature of 535-545° C., a bias voltage of about 600 V, a flow ratio of nitrogen to hydrogen of 1:3, an atmospheric pressure of 100 Pa, an ion nitriding time of 30 minutes, and an average thickness of about 2 μm of the white bright layer 50 formed on the surface of the stent.

After the ion nitriding step, a nitrogen valve is turned off, and an ion etching step would be started in the same equipment. At this moment, it is better to also turn off the bias power supply, and a mixed gas of argon and hydrogen at a flow ratio of 1:3 is fed in. When the mixed gas of argon and hydrogen is substantially stable, the bias power supply is activated, with an atmospheric pressure of 100 Pa, a stent temperature of 540-550° C. and a bias voltage of about 650 V. The gas is ionized at the high voltage, and a part of the white bright layer 50 having a high nitrogen content on the surface of the stent is sputtered or decomposed by the reduction capacity of hydrogen ions and the high-energy bombardment of argon ions. Meanwhile, as the surface temperature of the stent is relatively high and the concentration of nitrogen atoms on the surface is higher than that of the inside, a part of nitrogen atoms released from the white bright layer 50 continues to diffuse to the inside of the material, so that the diffusion layer 10 is further extended and the white bright layer 50 is reduced faster. Under the combined action of multiple factors, the purpose of removing the white bright layer 50 is finally achieved. The ion etching step is continuously performed for about 30 minutes, ensuring that the white bright layer 50 is completely removed. Then, the bias voltage is turned off, and the stent is cooled with the vacuum chamber and then taken out. The surface roughness of the ion-etched stent is about 0.05 μm, and the ion-etched stent is flatter in comparison to the boundary between the white bright layer 50 and the diffusion layer 10 after ion nitriding in FIG. 1. The lower surface roughness is advantageous to the surface polishing treatment, so the ion etching step makes the subsequent polishing treatment more easily achieve the mirror polishing effect.

Figure 4:
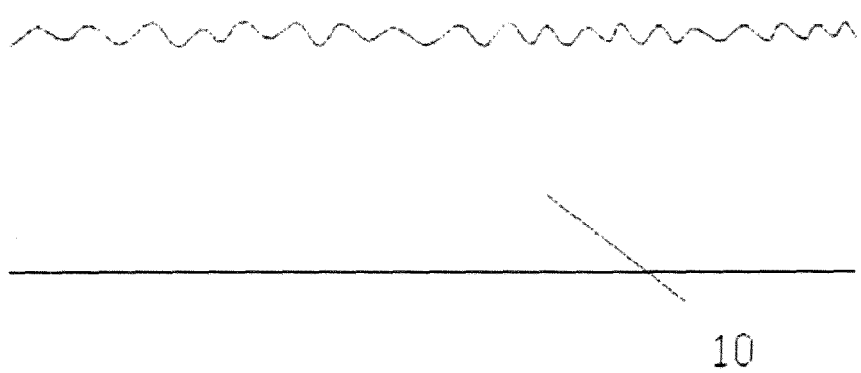
FIG. 4 is a cross-sectional diagram of a vessel stent after ion etching and polishing according to an embodiment of the present invention.

The next step is polishing mainly for purpose of making the surface of the stent smooth and bright. The mirror polishing effect might also be achieved by a conventional polishing method in the prior art, and this embodiment employs a normal-temperature chemical polishing method. When the stent is polished after ion nitriding and ion etching, a chemical polishing method might be directly used because the corrosion-resistant white bright layer has been substantially removed and the surface roughness reaches certain conditions. The stent is placed in the above chemical polishing solution, for example, a chemical polishing solution prepared from hydrogen peroxide having a volume concentration of 30%, hydrofluoric acid having a volume concentration of 40% and purified water at a ratio of 80:5:15. The stent was taken out after about 30-40 seconds under the same normal temperature conditions, then neutralized with the forgoing alkali, ultrasonically cleaned for two times with purified water with the time of each ultrasonic cleaning being 10 second, and finally dehydrated with absolute ethyl alcohol for storage. After the cleaning step, the wall thickness of the stent is reduced by about 25 μm (inner and outer walls are reduced by 15 μm and 10 μm, respectively) for purpose of achieve the approximate mirror polishing effect, the surface roughness Ra is below 0.01 μm, and only the diffusion layer 10 shown in FIG. 4 remains on the surface of the stent. To ensure the normal-temperature chemical polishing to achieve the mirror effect, considering the thickness reduction of the cleaned surface before ion nitriding and the removal of the white bright layer 50 having an average thickness of about 2 μm, the requirements may be met as long as the wall thickness of the pure iron tube is about 32 μm thicker than the wall thickness of the finished product stent.

In this embodiment, during ion nitriding, the temperature of the stent is about 535-545° C., the flow ratio of nitrogen to hydrogen is 1:3, the atmospheric pressure is 100 Pa, the bias voltage is about 600 V, and the time of ion nitriding is 30 minutes. Subsequently, ion etching is performed. Argon and hydrogen are fed in at a flow ratio of 1:3, the atmospheric pressure is 100 Pa, the temperature of the stent is 540-550° C., the bias voltage is about 650 V, and the time of etching is 30 minutes. The tests show that the harness value of the outer surface of the diffusion layer 10 is about 250HV0.01, and the radial strength is 65 KPa. The white bright layer on the surface of the stent is ion-etched and thus removed. The approximate mirror polishing effect may be achieved as long as the total thickness (removal amount) of the stent surface removed by the chemical polishing is about 25 μm, so that the surface roughness Ra is below 0.01 μm. This manufacturing method is easier to control product quality and production efficiency, and meets the mechanical performance and processing precision requirements for a bioabsorbable stent.

A surface drug loading treatment may be performed on the polished stent. The preparation of a drug coating solution should be performed in a glass container with a cover. Good stirring is provided by a magnetic stirrer and a polytetrafluoroethylene stirrer. Coating materials (the drug is sirolimus, and the carrier is polylactic acid) are accurately weighed and then added in the container, and a desired amount of tetrahydrofuran is weighed by a balance by the desired concentration and then added in the container. The magnetic stirrer is activated until the coating materials are totally dissolved. The stent after surface treatment is placed on a homemade spraying apparatus for coating. The coated stent is dried in a dryer at 50° C. The drug-coated iron alloy instrument is dense and uniform in surface, has consistent color and has a thickness of about 5 μm. The drug loading capacity is 140 μg/cm$^2$. After drug loading, a surface coating treatment may be performed in order to reduce the original thrombus nature of the surface. A high-molecular coating with negative electricity is first sprayed on the surface, and the stent is dipped in a chitosan solution for 3 seconds and then dipped in a heparin sodium solution for 3 seconds. The chitosan-heparin coating is dipped repeatedly for 8 times.

After the stent is clamped on a balloon catheter, the stent is vacuum packaged, and then sterilized for 8 hours with ethylene oxide. The storage life is 6 months.

Embodiment 2

According to a stent grid design in this industry, the surface of a pure iron tube is carved by lasers to pre-form a pure iron coronary stent having an outer diameter of 1.6 mm, an original wall thickness of 110 μm and a length of 18 mm. When this stent is balloon-dilated to 3 mm, the coverage rate of the metal grid on the surface of the stent to the side wall of the stent is about 13% Subsequently, the stent is treated by the following steps.

The same pure iron coronary stent is manufactured by the corresponding steps of Embodiment 1. The stent is cleaned and then processed by ion nitriding. In this embodiment, the following ion nitriding parameters are selected: a stent temperature of 530-540° C., a bias voltage of about 650 V, a flow ratio of nitrogen to hydrogen of 1:8, an atmospheric pressure of 50 Pa, an ion nitriding time of 60 minutes, and an average thickness of about 4-5 μm of the white bright layer 50 formed on the surface of the stent.

Figure 3:
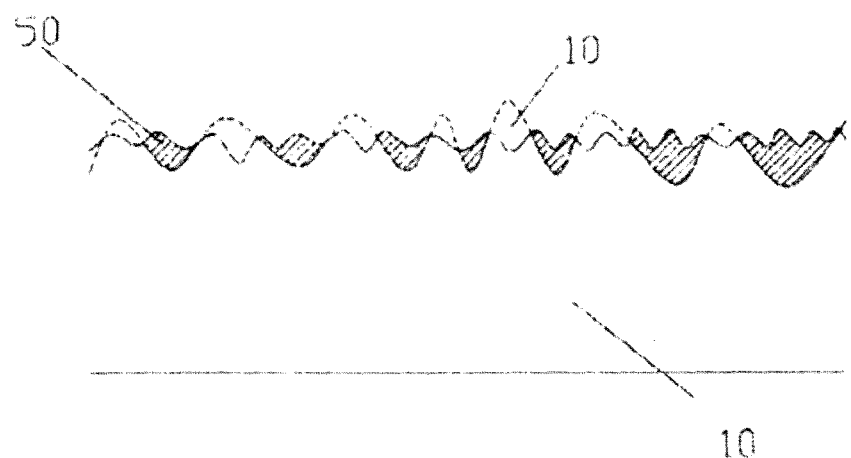
FIG. 3 is a schematic diagram of a change in cross section of a vessel stent after ion etching according to an embodiment of the present invention.

After the ion nitriding step, nitrogen is turned off, and an ion etching step is started. At this moment, the bias power supply is turned off, a mixed gas of argon and hydrogen is fed in at a flow ratio of 1:7, and the atmospheric pressure of 45 Pa. When the mixed gas of argon and hydrogen is substantially stable, the bias power supply is activated, with a bias voltage of 750 Pa and a stent temperature of 535-545° C. The bias voltage is turned off after the ion etching is performed for 50 minutes, and the stent is fully cooled and then removed from the vacuum chamber. A very thin (the average thickness was less than 1 μm) discontinuous white bright layer 50 (i.e., a compound layer) and a diffusion layer 10 remain on the surface of the stent. The partial cross section of the stent is shown in FIG. 3, where the portion of oblique line is the discontinuous high-nitrogen compound remained on the surface, and the portion of dashed line is a protruded portion of the diffusion layer 10 that has been ion-etched. The boundary between the white bright layer 50 and the diffusion layer 10 in FIG. 1 is not smooth, while the ion-etched surface in FIG. 3 becomes smoother, which is advantageous to the realization of mirror polishing effect.

The next step is polishing. In this embodiment, the equipment and parameters for polishing are the same as those in Embodiment 1. During chemical polishing, a part of the diffusion layer 10 is be corroded, and the few remaining parts (the portion of oblique line in FIG. 3) of the white bright layer 50 on the surface of the stent are also easy to corrode. However, the continuous white bright layer is difficult to remove by a chemical corrosion method at a normal temperature. At the end of the chemical polishing, the surface of the stent becomes smoother, the mirror polishing effect may be achieved, and only the diffusion layer 10 shown in FIG. 4 remains on the surface of the stent.

In this embodiment, the obtained stent has a wall thickness of 75 μm, which is reduced by 35 μm in comparison to the wall thickness of the original pure iron tube, the average hardness of the outer surface of the diffusion layer 10 is 260HV0.01, and the total thickness removed by the chemical polishing (removal amount) is about 26 μm for purpose of achieving the approximate mirror polishing effect, and the surface roughness Ra is below 0.01 μm. After the coronary stent is balloon-dilated to 3 mm, the radial strength is 140 kPa, which is improved by 30% in comparison to the radial strength of 108 KPa of a pure iron stent of the same design and size.

Embodiment 3

A pure iron coronary stent is manufactured by the corresponding steps of Embodiment 2. After cleaning, the stent is processed by ion nitriding. The ion nitriding parameters of this embodiment are substantially the same as those in Embodiment 2, and the ion nitriding time is also 60 minutes. The average thickness of the white bright layer 50 formed on the surface of the stent is about 4-5 μm. After the ion nitriding step, nitrogen is turned off, and an ion etching step is started. The ion etching parameters of this embodiment are substantially the same as those in Embodiment 2 except that the ion etching time is prolonged to 60 minutes. The bias voltage is then turned off, and the stent is fully cooled and then removed from the vacuum chamber. As the ion etching time is prolonged by 10 minutes in comparison to Embodiment 2, there is no white bright layer 50 (i.e., the compound layer) on the surface of the stent, so that it is more advantageous to the subsequent polishing. The next step is polishing. In this embodiment, the equipment and parameters for polishing are the same as those in Embodiment 1.

In this embodiment, the polished stent has a wall thickness of 75 μm, which is reduced by 35 μm in comparison to the wall thickness of the original pure iron tube, and the average hardness of the outer surface of the diffusion layer 10 is 260HV0.01. There is no white bright layer on the nitrided and ion-etched surface of the stent, the total thickness removed by the subsequent chemical polishing (removal amount) is about 25 μm for purpose of achieving the approximate mirror polishing effect, and the surface roughness Ra is below 0.01 μm, so that the mechanical performance and processing precision requirements for a bioabsorbable stent are met. After the coronary stent is balloon-dilated to 3 mm, the radial strength is 140 kPa, which is improved by 30% in comparison to the radial strength of 108 KPa of a pure iron stent of same the design and size.

The above data indicates that after the ion etching time is prolonged by 10 minutes, there is no residual white bright layer 50 on the surface of the stent and the surface roughness is about 0.05 μm, so it is indicated that the ion etching time of the stent may be selected according to the thickness and density of the white bright layer, and the thickness of density of the white bright layer increase with the ion nitriding time. The thicker and denser the white bright layer is, the longer the required ion etching time is. Generally, the ion etching time should be 80-110% of the ion nitriding time, so that the very thin (the thickness is less than 1 μm) discontinuous white bright layer remains on the surface of the stent or the white bright layer is completely removed. Thus, the mirror polishing effect may be achieved subsequently only by normal-temperature chemical polishing, and the mechanical performance and processing precision requirements for a bioabsorbable stent may be met.

Embodiment 4

A pure iron coronary stent is manufactured by the corresponding steps of Embodiment 2. After cleaning, the stent is processed by ion nitriding. In this embodiment, the following ion nitriding parameters are selected: a stent temperature of 510-520° C., a bias voltage of about 600 V, a flow ratio of nitrogen to hydrogen of 1:5, an atmospheric pressure of 70 Pa, an ion nitriding time of 100 minutes, and an average thickness of about 5 μm of the white bright layer 50 formed on the surface of the stent.

After the ion nitriding step, nitrogen is turned off, and an ion etching step is started. The bias power supply is turned off, and a mixed gas of argon and hydrogen is fed in. When the mixed gas of argon and hydrogen is substantially stable, the bias power supply is activated, with a flow ratio of 1:5, an atmospheric pressure of 60 Pa, a stent temperature of 515-525° C. and a bias voltage of about 700V. The bias voltage is turned off after the ion etching is performed for 100 minutes, and the stent is cooled and then removed from the vacuum chamber. There is no residual compound layer on the surface of the stent. The next step is polishing. In this embodiment, the equipment and parameters for the polishing are the same as those in Embodiment 1.

In this embodiment, the polished stent has a wall thickness of 75 μm, which is reduced by 35 μm in comparison to the wall thickness of the original pure iron tube, and the average hardness of the outer surface of the diffusion layer 10 is 290HV0.01. There is no white bright layer on the nitrided and ion-etched surface of the stent, the total thickness removed by the subsequent chemical polishing (removal amount) is about 25 μm for purpose of achieving the approximate mirror polishing effect, and the surface roughness Ra is below 0.01 μm, so that the mechanical performance and processing precision requirements for a bioabsorbable stent are met. After the coronary stent is balloon-dilated to 3 mm, the radial strength is 180 kPa, which is improved by 67% in comparison to the radial strength of 108 KPa of a pure iron stent of the same design and size.

In the treatment method of the present invention, an ion etching step may be employed after the ion nitriding step, and the two steps may be performed in situ in the same equipment as long as the equipment parameters are slightly adjusted, so that it is convenient for industrial application. In the ion etching step, nitrogen atoms continuously permeate the inside of the medical apparatus, and the corrosion-resistant white bright layer generated in the ion nitriding step may be effectively removed. The method also reduces the difficulty of the subsequent polishing step so that the normal-temperature chemical polishing easily achieves the mirror polishing effect and conforms more to the medical and production safety requirements, and the time it takes for the medical apparatus to be absorbed by the human body and the requirements for the hardness and strength are also ensured. For a corresponding component preformed from pure iron or iron alloy, the product quality may be well controlled as long as about 35 μm of polishing removal amount is reserved with regard to the thickness of the raw material.

The foregoing description merely shows preferred embodiments of the present invention and is not intended to limit the present invention. Any modification, equivalent replacement and improvement made within the spirit and principle of the present invention shall fall into the protection scope of the present invention.

The invention claimed is:

1. A manufacturing method of an iron-based alloy medical apparatus, comprising:
nitriding an iron-based alloy preformed unit at 350-550° C. for 30-100 minutes; and
ion etching the iron-based alloy preformed unit with an ion etching time of 80-110% of the nitriding time;
wherein the method further comprises a step of soaking the preformed unit in a chemical polishing solution for about 5-10 seconds before the nitriding; and, by volume, the chemical polishing solution comprises 75-85 parts of hydrogen peroxide having a volume concentration of 30% and 3-7 parts of hydrofluoric acid having a volume concentration of 40%.

2. The method of claim 1, wherein an outer layer thickness of 15-30 μm of the preformed unit is removed by the chemical polishing.

3. The method of claim 1, wherein the method further comprises a step of forming a drug-loaded coating on a surface of the polished preformed unit.

4. The method of claim 1, wherein the performed unit before the nitriding is 30-60 μm thicker than the polished preformed unit.

5. A manufacturing method of an iron-based alloy medical apparatus, comprising:
nitriding an iron-based alloy preformed unit at 350-550° C. for 30-100 minutes;
ion etching the iron-based alloy preformed unit with an ion etching time of 80-110% of the nitriding time; and
polishing the ion-etched preformed unit;
wherein the polishing is chemically polishing for 30-40 seconds; and by volume, a solution for the polishing comprises 75-85 parts of hydrogen peroxide having a volume concentration of 30% and 3-7 parts of hydrofluoric acid having a volume concentration of 40%.

6. The method of claim 5, wherein an outer layer thickness of 15-30 μm of the preformed unit is removed by the chemical polishing.

7. The method of claim 5, wherein the method further comprises a step of forming a drug-loaded coating on a surface of the polished preformed unit.

8. The method of claim 5, wherein the performed unit before the nitriding is 30-60 μm thicker than the polished preformed unit.

* * * * *